(12) United States Patent
Kobos et al.

(10) Patent No.: US 7,553,622 B2
(45) Date of Patent: Jun. 30, 2009

(54) PROCESS FOR PREPARING PROCESSED SAMPLE LIQUID SOLUTION FOR ELECTROPHORESIS

(75) Inventors: Robert K. Kobos, Wilmington, DE (US); Richard R. Reffuge, Bear, DE (US); Robert W. Kachelries, West Chester, PA (US); Miriam L. Ronchi, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 890 days.

(21) Appl. No.: 10/500,420

(22) PCT Filed: Feb. 25, 2003

(86) PCT No.: PCT/US03/07222

§ 371 (c)(1),
(2), (4) Date: Jun. 25, 2004

(87) PCT Pub. No.: WO03/072228

PCT Pub. Date: Sep. 4, 2003

(65) Prior Publication Data

US 2005/0029104 A1 Feb. 10, 2005

(51) Int. Cl.
*C12Q 1/68* (2006.01)
*C12N 1/06* (2006.01)

(52) U.S. Cl. .......................... 435/6; 204/450; 204/451; 204/456

(58) Field of Classification Search ........................ None
See application file for complete search history.

(56) References Cited

U.S. PATENT DOCUMENTS

| | | | |
|---|---|---|---|
| 4,473,452 A | 9/1984 | Cantor et al. | |
| 5,122,248 A | 6/1992 | Karger | |
| 5,167,790 A | 12/1992 | Carle et al. | |
| 5,182,242 A | * 1/1993 | Marler | 502/66 |
| 5,595,876 A | 1/1997 | Rakestraw | |
| 6,261,842 B1 | 7/2001 | Handelsman | |

OTHER PUBLICATIONS

Biavati et al. Current Microbiology vol. 24:285-287. 1992.*
Durmishkhan Turabelidze et al., Improved Pulsed-Field Gel Electrophoresis for Typing Vancomycin-Resistant *Enterococci*, Journal of Clinical Microbiology, vol. 38(11):4242-4245, Nov. 2000.
Romesh K. Gautom, Rapid Pulsed-Field Gel Electrophoresis Protocol for Typing of *Escherichia coli* O157:H7 and Other Gram-Negative Organisms in 1 Day, Journal of Clinical Microbiology, vol. 35(11):2977-2980, Nov. 1997.
Yongseong Kim et al., Rapid Pulsed Field Capillary Electrophoretic Separation of Megabase Nucleic Acids, Anal. Chem., vol. 67:784-786, 1995.
John Maule, Pulsed-Field Gel Electrophoresis, Molecular Biotechnology, vol. 9:107-126, 1998.
E. Lai et al., Pulsed Field Gel Electrophoresis, BioTechniques, vol. 7(1):34-42, 1989.
Fangman W L: "Separation of Very Large DNA Molecules by Gel Electrophoresis" Nucleic Acids Research, IRL Press LTD., Oxford, GB, vol. 5, No. 3, Mar. 3, 1978, pp. 653-665.
Serwre P: "Electrophoresis of Duplex Deoxyribonucleic Acid in Multiple-Concentration Agarose Gels: Fractionation of Molecules With Molecular Weights Between 2×106 and 110×106" Biochemistry, American Chemical Society. Easton, PA, US, vol. 19, 1980, pp. 3001-3004.
Schwartz D C et al: "New Techniques for Purifying Large DNAs and Studiyng Their Properties and Packaging" Cold Spring Harbor Symposia on Quantitative Biology, New York, NY, US, vol. 47, No. 1, 1983, pp. 189-195.
Anonymous: "CHEF-DR II Pulsed Field Electrophoresis Systems" Internet Article, Online 1992, pp. 1-46, XP002326532 Retrieved from the Internet: URL: http://www.biorad.com/cmc_upload/0/000/013/015/M1703729B.pdf> (no longer functional).
Guzman P, Ecker Jr (1988) Development of large DNA methods for plants: molecular cloning of large segments of *Arabidopsis* and carrot DNA in yeast. Nucleic Acids Res 16:11091-11105.

* cited by examiner

*Primary Examiner*—Gary Benzion
*Assistant Examiner*—Heather G Calamita (57) ABSTRACT

A process for preparing a processed sample liquid solution for gel electrophoresis, comprising (a) treating a sample comprising a cell suspension in a non-shearing manner to produce a processed sample liquid solution comprising a mixture of DNA fragments extracted from the cell suspension, wherein at least one of the DNA fragments is greater than 200 kilobase pairs and (b) transferring the processed sample liquid solution in a non-shearing manner directly to an electrophoresis medium for conducting electrophoresis.

23 Claims, 6 Drawing Sheets

PROCESS FOR PREPARING PROCESSED SAMPLE LIQUID SOLUTION FOR ELECTROPHORESIS

FIELD OF THE INVENTION

This invention relates to the field of gel electrophoresis. More specifically, this invention relates to the preparation of a processed sample liquid solution, and to separation of DNA fragments of the sample by electrophoresis, particularly pulsed-field gel electrophoresis.

BACKGROUND OF THE INVENTION

A major tool in molecular biology and related fields is electrophoretic separation. In this process, mixtures of macromolecules, e.g., proteins, DNA, or RNA, are moved through a sieving medium, such as a gel, by an electric field. Electrophoretic separation enables qualitative analysis, separation, recovery, and purification of macromolecules.

Nucleic acid molecules have one negative charge for each nucleotide. As a result, the charge-to-mass ratio is constant for DNA of various lengths and an electric field alone would not perform separation of DNA. In a porous medium, however, larger DNA molecules have greater difficulty traversing the enmeshing medium and move slower than smaller DNA molecules, thereby causing separation of DNA molecules of varying length. This separation effect is size limited, however, and conventional gel and capillary electrophoresis separation of DNA molecules is generally limited to sizes smaller than 50 kilobase pairs (kbp).

U.S. Pat. No. 4,473,452 to Cantor teaches that electrophoresis of very large molecules can succeed by using alternating transverse electric fields. This method is known as pulsed-field gel electrophoresis (PFGE). It is generally believed that the chains of molecules presented to the PFGE gel are oriented and re-oriented by the fields, allowing the longer chains to traverse the gel medium without clogging the passages. In addition, the longer the chains are, the greater is the relaxation time involved in the changes of orientation. As a result, the smaller chains move into and through the gel matrix much more readily than the larger chains. As described by E. Lai, et al. ("Pulsed-field Gel Electrophoresis," *Bio Techniques*, 7, pp. 34-42, 1989), the alternating electric fields can be applied in a number of orientations, giving rise to several variations of the PFGE method, e.g., field inversion gel electrophoresis (FIGE), clamped homogeneous electric fields (CHEF) electrophoresis, and pulsed homogeneous orthogonal field gel electrophoresis (PHOGE). The pulsed-field technique has also been applied to capillary electrophoresis for the separation of large DNA fragments as described by Kim and Morris ("Rapid Pulsed-field Capillary Electrophoretic Separation of Megabase Nucleic Acids," *Anal. Chem.* 67, pp. 784-786, 1995).

One of the primary applications of PFGE is the molecular typing of bacteria. In this methodology, bacterial cells, imbedded in an agarose plug, are treated to lyse the cells and remove or destroy cellular proteins. The released chromosomal DNA is then treated with a restriction endonuclease enzyme that cleaves infrequently to cut the DNA into large fragments, typically between 50 and 800 kbp in size. These large DNA fragments are separated using PFGE to yield a DNA fingerprint which can be used to identify the bacterium at the species and sub-species level and to differentiate among related bacteria.

While extremely effective for the molecular typing of bacteria and other microbes, PFGE has the major disadvantage of an extremely time-consuming sample treatment process, wherein three to four days is not uncommon. One reason the sample treatment process is time-consuming is the need to protect the fragile DNA molecules from unintended mechanical breakage. Traditional methods for sample preparation in which the end product is DNA in solution are unsuitable for PFGE because large DNA molecules are susceptible to shearing forces leading to mechanical breakage. John Maule, "Pulsed-Field Gel Electrophoresis", *Molecular Biotechnology*, Volume 9, 1998, pp. 107-126.

The method of U.S. Pat. No. 4,473,452 to Cantor avoids mechanical breakage of the long DNA molecules by incorporating the bacterial cells into molded inserts (also known as "plugs"), typically made of an agarose gel, and performing the sample treatment on the entrapped cells. This sample treatment includes lysis of the bacterial cells, enzymatic digestion of cellular proteins, and digestion of the DNA to produce fragments of various sizes using an appropriate restriction endonuclease enzyme. The treated plugs are then fitted into wells molded into the electrophoresis gel and PFGE is performed, resulting in a fingerprint pattern for the bacterium. By using the plugs, the DNA molecules can be extracted from the cell and digested in a controlled manner, without unwanted mechanical breakage of the DNA.

Molecular typing of bacterial cells by PFGE has typically been achieved using plugs. In this process, the cells or spheroplasts are suspended in gel (usually agarose) and then poured into molds to form the plugs. The sample treatment steps of lysis, deproteinization, and digestion are performed on the cells, embedded in the agarose plugs, as follows. First, the sample plugs are placed in a solution containing a lysing agent, e.g., lysozyme, and incubated at the appropriate temperature overnight. The lysing solution is then removed and the plugs are washed with buffer. A protease-containing solution, e.g., Proteinase K, is next added to digest proteins and the plugs are incubated overnight at the appropriate temperature. The next day, the protease solution is removed, and the plugs are washed several times with wash buffer. The plugs are washed with diluted wash buffer and then with the restriction enzyme buffer. A suitable restriction endonuclease-containing solution is then added to the plugs and the plugs are incubated overnight at the appropriate temperature. The next day, the restriction endonuclease solution is removed, and the plugs are washed with the wash buffer. A final wash is performed with the electrophoresis buffer, e.g., 0.5× tris-borate-EDTA (TBE) buffer. The plugs are then inserted into matching wells formed in a gel slab by a suitable comb and the pulsed-field electrophoretic separation is carried out. Care must be taken at every step to ensure that the plugs are not damaged in the process.

This sample plug treatment protocol avoids mechanical breakage in handling long and fragile DNA molecules. However, it makes sample treatment very tedious and time consuming, and the results are operator dependent. Sufficient time is required for diffusion of reagents into the agarose plugs. Moreover, the use of plugs makes automation of the sample preparation process very difficult, if not impossible. It is believed that there are no known reports of an automated sample treatment process for bacterial typing using PFGE.

Some practitioners have evolved one day protocols for PFGE employing plugs. But these protocols are often labor intensive and require highly skilled personnel. For example, Turabelidze, et al. ("Improved Pulsed-Field Gel Electrophoresis for Typing Vancomycin-Resistant Enterococci," *J. Clinical Microbiology* November 2000, p. 4242-4245) describes a rapid protocol for sub-typing vancomycin-resistant enterococci in approximately one day. Gautom ("Rapid Pulsed-Field Gel Electrophoresis Protocol for Typing Of *Escherichia coli* 0157:H7 and Other Gram-Negative Organisms in 1 Day," *J. Clin. Microbiol.* 35, November 1997, pp. 2977-2980) teaches a standardized protocol that is done in one day using bacterial cells directly from the culture plates, shortening cell lysis and deproteinization, using preheated buffer, and shorter restriction digestion times. In these more rapid methods, nevertheless, plugs are employed.

It has been reported in the CHEF-DR® II Pulsed-field Electrophoresis Systems Instruction Manual and Applications Guide from Bio-Rad Laboratories that liquid samples can be transferred and separated using PFGE when working with DNA in the size ranging from 50 kbp up to 200 kbp by taking special precautions not to mechanically break the DNA molecules. Specifically, the use of a pipet tip with a large opening is recommended. There is believed to be no known report of a non-shearing treatment and transfer of a liquid sample having DNA lengths greater than 200 kbp. For bacterial typing, the DNA fragments of interest often are greater than 200 kbp and typically range from 50 kbp to 1000 kbp, and are even greater than 1000 kbp in some instances. Therefore, for bacterial typing, sample plugs have been required to prevent mechanical breakage of the DNA molecules during sample treatment and gel loading.

There remains a need to reduce the sample treatment time required in the molecular typing of bacteria using PFGE. In addition, there is a need to eliminate the use of sample plugs in PFGE without causing unwanted mechanical breakage of the DNA molecules. There also is a need to treat and transfer bacterial samples for PFGE with a minimum degree of operator dependence by automating the sample treatment process.

SUMMARY OF THE INVENTION

The present invention provides a process for preparing a processed sample liquid solution for electrophoresis that eliminates the use of gel plugs. The processed sample liquid solution comprises a mixture of DNA fragments wherein at least one of the DNA fragments is greater than 200 kilobase pairs. The process comprises the steps of:

(a) treating a sample comprising a cell suspension in a non-shearing manner to produce a processed sample liquid solution comprising a mixture of DNA fragments extracted from the cell suspension, wherein at least one of the DNA fragments is greater than 200 kilobase pairs; and (b) transferring the processed sample liquid solution in a non-shearing manner directly to an electrophoresis medium for conducting electrophoresis.

The invention also provides a method for separating a mixture of DNA fragments from a sample. This method comprises the steps of:

(a) treating a sample comprising a cell suspension in a non-shearing manner to produce a processed sample liquid solution comprising a mixture of DNA fragments extracted from the cell suspension, wherein at least one of the DNA fragments is greater than 200 kilobase pairs;

(b) transferring the processed sample liquid solution in a non-shearing manner directly to an electrophoresis medium for conducting electrophoresis; and (c) separating the mixture of DNA fragments by conducting electrophoresis.

In one embodiment of the invention, the DNA fragments are 50 kbp to 1000 kbp. In another embodiment, at least one of the DNA fragments is greater than 225 kilobase pairs, is greater than 250 kilobase pairs, or is greater than 300 kilobase pairs.

The cell suspension can comprise one or more cells that are suspended in a lysis buffer. In one embodiment, the cell suspension is a bacterial cell suspension.

The step of treating the cell suspension can comprise the steps of subjecting the cell suspension to lysis, deproteinization, and digestion. The treatment step can be automated or manual. In the automated treatment step, the treatment of the cell suspension, including reagent additions and incubations, is achieved using an automated apparatus. The step of transferring the processed sample liquid solution to the well of the electrophoresis gel can be automated or manual.

The electrophoresis medium can be an electrophoresis gel, including the electrophoresis gels used for pulsed-field gel electrophoresis. The electrophoresis medium can also be a viscous sieving solution other than a gel, including the viscous solutions used for pulsed-field capillary electrophoresis. In a preferred embodiment, the processed sample solution is transferred to a well of the pulsed-field electrophoresis medium.

BRIEF DESCRIPTION OF THE DRAWING

The invention is better understood from the following detailed description of preferred embodiments of the invention when read in connection with the accompanying drawing. It is emphasized that, according to common practice, the various features of the drawing are not to scale, unless otherwise indicated herein. On the contrary, the dimensions of the various features are arbitrarily expanded or reduced for clarity. Included in the drawing are the following figures:

FIG. 3A to FIG. 3D are sequential, perspective views of an apparatus assembled to carryout the process of the invention.

DETAILED DESCRIPTION OF PREFERRED EMBODIMENTS OF THE INVENTION

Described herein is a process for treatment of a sample comprising a cell suspension, such as a bacterial cell suspension, and delivering the resulting processed sample liquid solution to an electrophoresis medium. This methodology is particularly useful for the automation of sample treatment for molecular typing of bacteria using pulsed-field gel electrophoresis (PFGE).

Contrary to standard operating procedures for sample treatment of bacterial cells for molecular typing using PFGE as hitherto performed, it has been discovered that the prepared molecular chains of DNA ("DNA molecules") can be handled in a liquid medium, unsupported by a gel matrix such as gel plugs. In accordance with the invention, the cell suspension is treated to produce a processed sample liquid solution comprising a mixture of DNA fragments wherein at least one of the fragments is greater than 200 kbp. Both the treatment of the cell suspension, which includes lysis, deproteinization, and digestion, and the transfer of the resulting processed sample liquid solution to the electrophoresis medium are undertaken in a non-shearing manner, since it is critical that the DNA molecules do not become fragmented due to unintended mechanical breakage.

By a "non-shearing manner" is meant that the forces acting on the DNA molecules during both treatment of the cell suspension and transfer of the processed sample liquid solution to the electrophoresis medium are minimized to prevent mechanical breakage of the DNA molecules. Mechanical breakage means that the DNA molecules are randomly fragmented or sheared by physical forces exerted upon the molecules. These forces include shear, tensile, and torsional forces. This mechanical breakage is distinctly different than the very specific DNA cleavage that is catalyzed by restriction endonuclease enzymes, which results in the desired DNA fragment pattern. If mechanical breakage of the DNA does occur, such breakage can be detected on the gel image following the separation of the restriction fragments by electrophoresis, such gel image having a loss of DNA bands and the appearance of a smear in the sample lanes.

The forces causing mechanical breakage of DNA molecules and the degree of sensitivity of the DNA molecules to such forces are readily apparent to those skilled in the art. Typically, larger DNA molecules are more fragile or delicate and tend to mechanically break more readily than smaller fragments. In the examples provided herein, the DNA size range utilized was between 50 kbp and 700 kbp since this size range is typical of that encountered in the molecular typing of bacteria.

One factor that particularly influences DNA breakage is the viscosity of the solutions delivered to treat the sample, and the viscosity of the processed sample liquid solution itself. Higher viscosity results in a higher force during reagent delivery and mixing and, therefore, increases DNA mechanical breakage. The viscosity of the reagent solutions used in the examples was between 1.17 and 3.44 cP (centipoise), measured at 25° C.

Another factor influencing mechanical breakage of the DNA is the geometry of the system, which includes the inner diameter and geometry of the pipet tip that delivers the reagents to the sample and the processed sample liquid solution to the electrophoresis gel, the size and shape of the sample well used to contain the sample during the addition of the lysis, deproteinization, and digestion reagents, and the position of the pipet tip in the sample well during reagent delivery. The geometry of the system can be configured, in conjunction with other factors that potentially cause mechanical breakage, to prevent DNA breakage. For example, a pipet tip with a larger inner diameter will typically result in less DNA breakage than a pipet tip with a small inner diameter.

Figure 1:
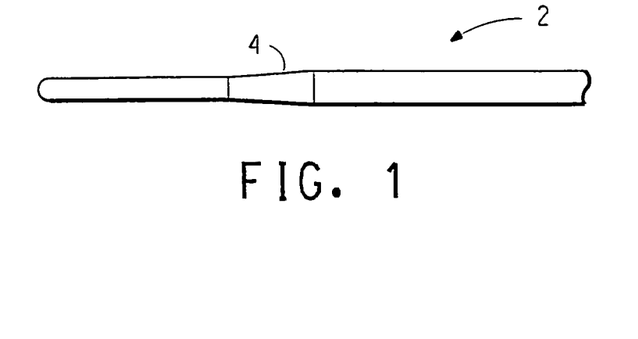
FIG. 1 is an elevational drawing of a pipet that can be used in the process of the invention.
Figure 2:
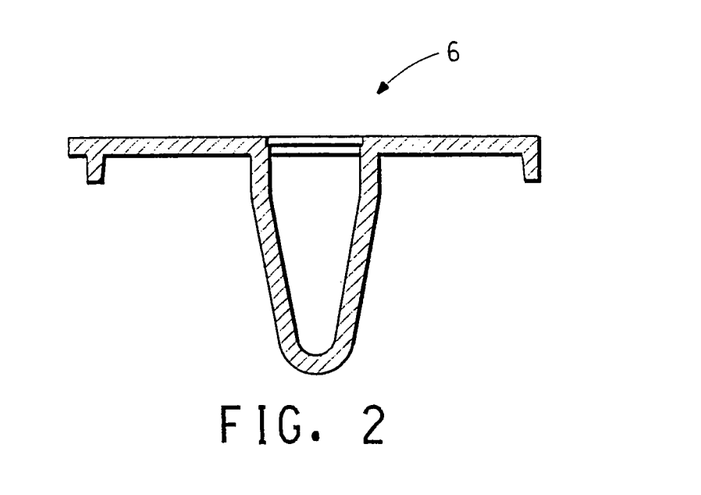
FIG. 2 is a cross sectional drawing of a sample carrier suitable for the invention.

A schematic representation of a pipet tip 2 that can be used in the present invention is shown in FIG. 1. In one embodiment of the invention, the tip has a length of 141.0 mm +/−0.25 mm, a tip inner diameter (ID) of 0.50 mm +/−0.10 mm below the tapered region 4, and an ID of 1.60 mm +/−0.10 mm above the tapered region. The geometry of a suitable sample well 6 is depicted in FIG. 2. In the examples detailed below, the pipet tip was positioned beneath the surface of the liquid in the center of the sample well, approximately 3-4 mm from the bottom of the well, for all of the reagent deliveries.

Yet another factor influencing mechanical breakage of DNA molecules is the velocity and acceleration of reagent delivery and sample mixing. The velocity and acceleration must be controlled to prevent DNA breakage.

The invention includes the step of (a) treating a sample comprising a cell suspension in a non-shearing manner to produce a processed sample liquid solution comprising a mixture of DNA fragments extracted from the cell suspension, wherein at least one of the DNA fragments is greater than 200 kilobase pairs. This treating step can be conducted following methods of extracting DNA in situ taught in U.S. Pat. No. 5,595,876 to Rakestraw, hereby incorporated by reference in its entirety.

These methods include the steps of:

(i) thermally treating the cells of the microorganism to deactivate the endogenous nuclease activity associated with the cells;

(ii) lysing the microorganism cells to release the component DNA and incubating the DNA to render the DNA amenable to subsequent enzymatic action; and (iii) thermally treating the DNA to denature remaining nucleases and proteases thereby deactivating any residual nuclease and protease activity.

This treating, as taught in U.S. Pat. No. 5,595,876 to Rakestraw, can optionally further include the step of (iv) further enzymatic modification of the DNA in the same reaction vessel. Following extraction, the DNA is then enzymatically digested in situ. One example is the digestion of the lysate with the restriction endonuclease EcoRI to generate a spectrum of DNA fragments.

This method, which includes (A) lysis to break open the cells, (B) deproteinization to destroy cellular proteins, and (C) digestion (with a restriction enzyme) to cut the DNA into fragments, is referred to herein as "LDD."

In the automated pipetting examples below (Examples 1-4), the reagent delivery parameters were optimized using the lysis, deproteinization, and digestion (LDD) module of the RiboPrinter® Microbial Characterization System available from Qualicon, Inc. All mixing steps were eliminated and the velocity and acceleration parameters for reagent delivery were reduced from the default parameters of the RiboPrinter® System. Example 5 is a comparative example that demonstrates mechanical breakage of the DNA when the default RiboPrinter® System pipetting parameters were used.

Reagent mixing in the process of the invention occurs via the agitation resulting from reagent delivery and by diffusion. Although the sample liquid could be mixed gently by aspiration, this increases the chances of mechanical breakage of the DNA and it has been discovered that such mixing was unnecessary. The optimum parameters for reagent delivery were determined empirically by varying the reagent delivery velocity and acceleration rates and observing the mechanical breakage that resulted on the gel image following electrophoresis, as described in Example 4. In Example 4, it was discovered that a reagent delivery velocity of 38 µL/sec and acceleration of 200 µL/sec$^2$ gave consistently low DNA breakage. Higher velocities, up to 581 µL/sec with an acceleration of 12800 µL/sec$^2$, could be used, but the results were not consistent, i.e., mechanical breakage was observed on some runs, but not on others. The transfer of the processed sample liquid solution to the electrophoresis medium is a critical step in the process because it is the only time that the DNA is aspirated into a pipet tip. The parameters used in the transfer of the sample liquid solution to the electrophoresis medium can be determined by routine experimentation.

The term "electrophoresis medium" includes those media used for electrophoretic separation. Electrophoresis media, as used herein, includes electrophoresis gels and non-gel viscous solutions that provide the sieving properties necessary to conduct electrophoretic separation.

Manual Process Treatment of Sample

As demonstrated below in Example 6, it was also discovered that substantially non-shearing conditions can be achieved by manual pipetting using a very slow delivery speed. In this case, the reagent deliveries were made to the sample well with the pipet tip placed against the side of the well above the sample to level. Although good results can be obtained with the manual technique, it is onerous and requires a patient operator, so it is recognized that the process is best performed by automated or mechanical means to insure reproducibility, ease of operation, and mechanical integrity of the DNA fragments.

The manual process can be performed as follows. First, bacterial cells are grown on an appropriate agar medium such as brain heart infusion (BHI) agar. Next, cells that have formed a solid lawn in the incubated agar medium are picked using an autoclaved colony pick and are transferred into a microcentrifuge tube held in a sample rack. The cells are then mixed with sample buffer (e.g., a hypotonic solution having an EDTA concentration between about 5 mM and 30 mM) with a vortexer.

The number of picks needed to give the optimum cell concentration can be determined empirically or by measuring the cell concentration by methods well known in the art, e.g., an optical density measurement or by counting cells using a hemocytometer. 30 μL of the sample liquid is then added to each well of the RiboPrinter® System sample carrier. Next, the sample carrier is placed in the heat treatment station of the RiboPrinter® System, which functions as a heating block to heat the samples to a temperature of about 80±2° C. for about 10 min to deactivate endogenous nuclease activity and to kill the cells.

After the samples cool, the sample carrier is loaded onto the RiboPrinter® System, which serves as a computer-controlled heating block for the manual process. Then, the lysing agent achromopeptidase (ACP) is added to each sample by very slowly pipetting the solution down the side of the sample wells. In this way, the sample is not agitated, and no mechanical breakage of the DNA results. It is possible to mix the samples by very slowly aspirating the sample liquid into the pipet tip and then returning the sample liquid to the sample well by pipetting down the wall using a pipet tip that has been cut-off to yield a larger opening, although such mixing is not required. ACP, in addition to serving as the lysing agent, also serves as the deproteinization reagent because it possesses proteolytic activity in addition to its lytic activity. The samples are then incubated at a suitable temperature, generally 37° C., for a time sufficient to lyse the cells and digest cellular proteins, typically 20 min to one hour. After this incubation, the samples are heated 70° C. to 75° C. for 15 min to 30 min to inactivate the ACP. Then, the appropriate restriction endonuclease enzyme is added to the samples in the manner described above. The samples are incubated at a suitable temperature for the restriction enzyme used. The incubation time depends on the restriction enzyme activity and the type of sample. Typically, the incubation time ranges from 1 hour to 4 hours, although longer times can be used, if necessary, to obtain complete digestion of the DNA.

Loading buffer is then manually pipetted slowly down the side of the sample wells to densify the samples for gel loading. The samples are mixed gently as described above. The samples are then added to the wells of the electrophoresis gel using the gentle pipetting method described above. The PFGE can then be run according to standard procedure.

Automated Process Treatment of Sample

Although treatment of the sample can be done manually, it is preferable to automate treatment steps to obtain the most reproducible results. FIG. 3A to FIG. 3D consecutively show a method in accordance with U.S. Pat. No. 5,595,876 to Rakestraw as applied to the instant invention, using an apparatus adapted from that of the aforementioned RiboPrinter® System. What cannot be seen, of course, is the restructured software that ensures minimal mechanical breakage of the DNA molecules. Although the process using the Ribo-Printer® System is described for purposes of illustration, one skilled in the art will recognize that any computer-controlled solution delivery apparatus with temperature control could be used to carry out the automated process of the instant invention.

Figure 3A:
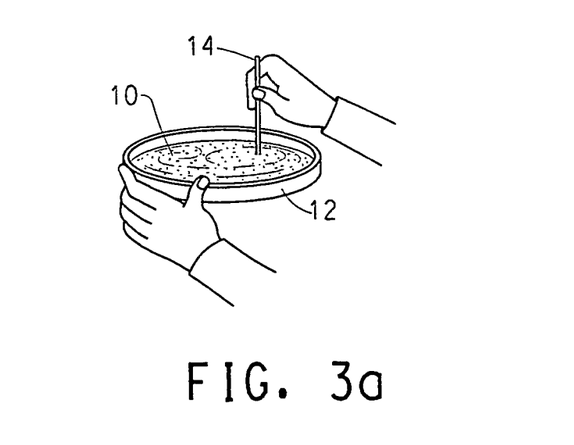
Figure 3B:
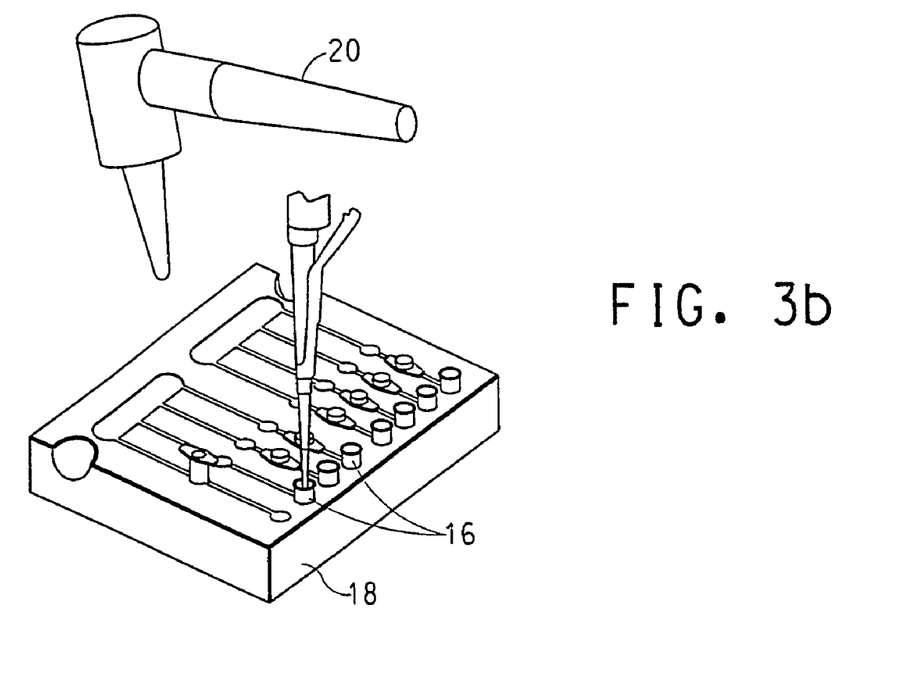
Figure 3C:
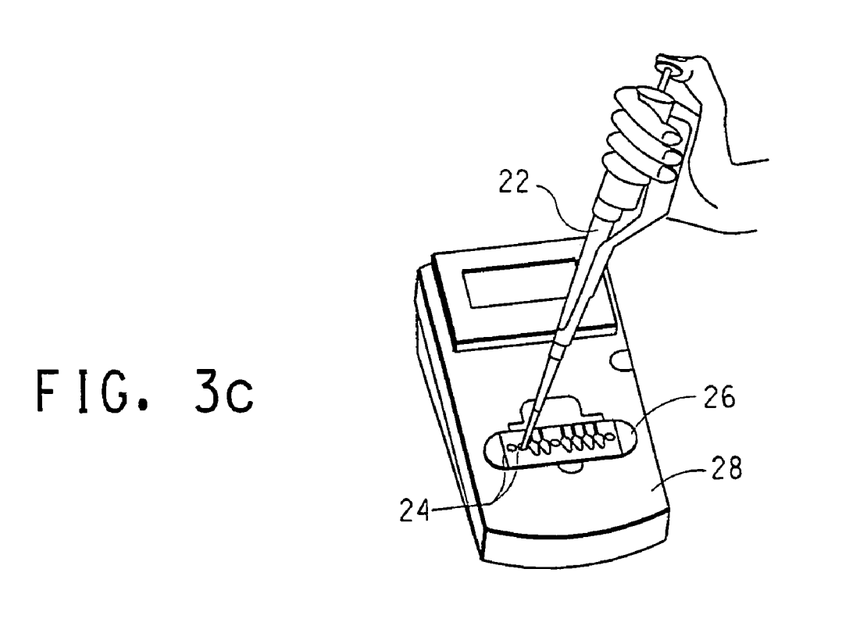

In FIG. 3A, a sample 10 is picked from petri dish 12 using pick 14 and transferred to a tube 16, containing a hypotonic, EDTA-containing buffer solution, held in rack 18 shown in FIG. 3B. The sample liquid is mixed using a vortexer 20 such as the Biovortexer obtainable from Biospec Products of Bartlesville, Okla. Referring next to FIG. 3C, the sample liquid is transferred using pipet 22 to one of the wells 24 in sample carrier 26 held in heat treatment station 28. A suitable heat treatment station may be obtained from Qualicon, Inc. The wells 24 are capped to prevent evaporation. The heat treatment station 28 is activated and performs the time and temperature regimen, described above, to deactivate nucleases and inactivate the cells.

Figure 3D:
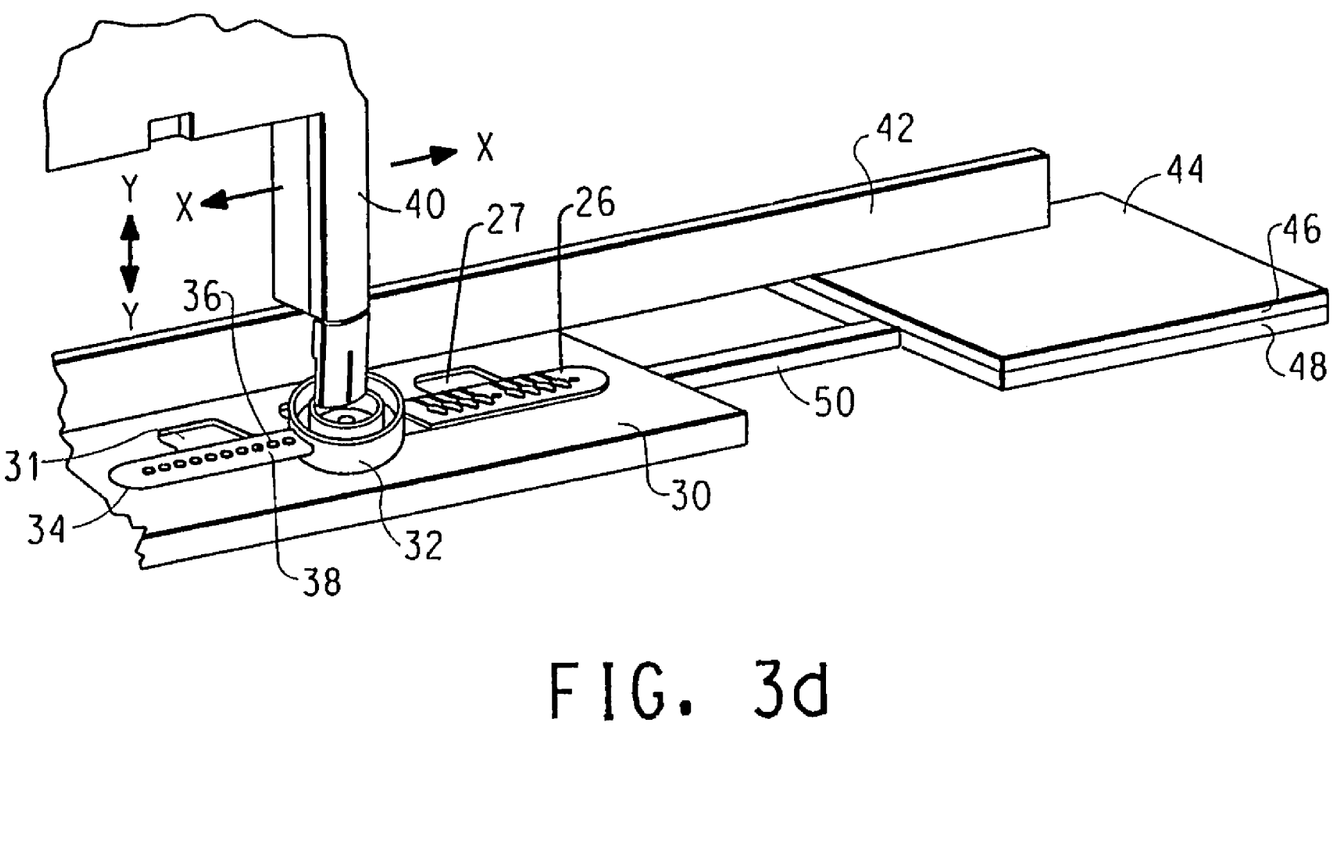

The sample carrier 26 is then placed in a cavity 27 in sample prep unit 30 as shown in FIG. 3D. Cavity 31, which is in line with cavity 27 and separated by wash unit 32, includes a DNA prep pack 34. The DNA prep pack contains all the reagents required for the lysis, deproteinization, and digestion treatment, including an ACP tablet, buffer for the restriction enzyme, and loading buffer. All these reagents are contained in wells sealed by a cover 38 which is made from a material that is readily pierced, such as foil. The appropriate restriction enzyme is contained in vial 36, which is inserted into an opening in the DNA prep pack. Also in line is traveler 40 which is controllably traversed along a line in accordance with arrows X-X by means not shown along a control arm 42 between the sample prep unit 30 and the gel box 48 containing a gel 44 up to a gel line 46. The gel box 48 and sample prep unit 30 can be fixed together by an arm 50. Within traveler 40 is a pipet, also not shown, which moves controllably in the direction indicated by the arrows Y-Y orthogonal to X-X. These motions are computer directed. The pipet is in fluid communication with sources of wash fluid and pumping means to aspirate and eject regulated small amounts of fluid.

In use, after the carrier 26 is loaded into cavity 27, the system controlling traveler 40 is actuated. The pipet is moved over the well in the prep pack that contains the ACP and a volume of water is added to re-hydrate the reagent. The solution is mixed by aspiration. Then, a selected aliquot of the ACP solution is aspirated into the pipet. Traveler 40 then moves over a selected well 24 in carrier 26, moves down to pierce the cap, and injects the aliquot into the well 24. The rate of injection is selected to minimize the force on the fluid handled to prevent mechanical breakage of the DNA molecules. Traveler 40 is then moved over wash station 32, the pipet is lowered and the inside and outside of the pipet tip is cleansed. This process is repeated for each sample. The samples are incubated in the presence of the ACP solution for a time sufficient to lyse the cells and inactivate internal cellular degradative factors, typically 20 min to 60 min. The samples are then heated to a temperature between 70° C. and 75° C. for a time sufficient to inactivate the remaining protease and nuclease activity, approximately 30 min. The samples are then cooled to the appropriate temperature for the restriction enzyme digestion.

The traveler is then moved over the appropriate well in prep pack 34 and downwardly through the cover 38 and into the selected buffer (at a 10× concentration) for the restriction enzyme. The buffer is then added to the vial containing the restriction enzyme and the solutions are mixed by aspiration. Typical restriction enzymes used for the molecular typing of bacteria using pulsed-field gel electrophoresis include, for example, XbaI, SfiI, SmaI, NotI, ApaI, and AscI. The enzyme selected controls digestion to produce DNA fragments having a length from about 50 kbp to about 800 kbp.

The restriction enzyme is then carried back to the selected well 24 and injected at a rate controlled to limit mechanical breakage of the DNA molecules. The samples are not mixed after the addition of the reagents. The wash and aspirate routine is repeated as needed until all ingredients required are added to the wells 24. In one embodiment, eight samples may be worked on in order. The wells 24 are then subjected to a controlled time at a selected temperature by means not shown. Finally, the loading buffer solution is added to each sample, as described above for the preceding reagents, to densify the samples to enable loading into the submerged gel. Then traveler 40 is actuated to remove a portion of the processed sample liquid solution from the wells 24 and inject, in a non-shearing manner, the contents into selected molded-in wells in the electrophoresis gel which are located in the line of traversal of traveler 40. Alternatively, this sample transfer to the electrophoresis gel can be done by gentle, manual pipetting. The electrophoresis gel is submerged in an electrophoresis buffer, e.g., 0.5× tris-borate-EDTA (TBE) buffer, during loading of the samples. Suitable pipet washing between well attendance is carried out to prevent cross-contamination of the samples.

Thus, the step of treating the sample can be performed in a single reaction vessel in an apparatus that is part of the RiboPrinter® Microbial Characterization System available from Qualicon, Inc., Wilmington, Del. The apparatus for automated sample treatment for pulsed-field gel electrophoresis of the invention can comprise a computer-directed automated apparatus for performing, in a substantially non-shearing manner, lysis, deproteinization and digestion, in accordance with processes of Rakestraw in U.S. Pat. No. 5,595,876, on a sample liquid comprising a bacterial cell suspension of the bacterial target in a lysis buffer to produce a processed sample liquid solution, containing fragments of the DNA of said target; said preparative apparatus optionally operatively associated with computer-directed, automated, liquid-transfer apparatus for transferring the said processed sample liquid solution in a substantially non-shearing manner to at least one well prepared in a gel slab in an associated, pulsed-field gel electrophoresis apparatus.

In one embodiment, the heat treatment station is separated from the main apparatus of the RiboPrinter® System. Separating the heat treatment station from the main apparatus of the RiboPrinter® System permits confining the handling of viable pathogens to a biological safety level 2 (BSL2) laboratory ("BioSafety in Microbiological and Biomedical Laboratories," U.S. Department of Health and Human Services, CDC/HIN, U.S. Government Printing Office; $2^{nd}$ ed., May, 1988 HHS Publication No. (NIH) 88-8395) and permits conveniently locating the major processing steps in general laboratory space.

EXAMPLES

In the examples, the reagent delivery and sample transfer parameters were optimized based on the specified conditions. For other DNA fragment sizes, reagent viscosities, and system geometries, these reagent delivery and sample transfer parameters can be determined by routine experimentation, as described above.

Example 1

Automated Treatment of Bacterial Cells Using Optimized Pipetting Parameters

In this example, all the pipetting, with the exception of the initial preparation of the cell suspension and the loading of the processed sample liquid solutions into the electrophoresis gel, was done in an automated manner using a separate lysis, deproteinization, and digestion (LDD) module from the RiboPrinter® Microbial Characterization System. A new LDD protocol was written specifically for the PFGE sample treatment, wherein the software was modified to reduce the speed at which the reagents were delivered to the samples to minimize forces that cause mechanical breakage of DNA molecules. Specifically, the reagent delivery velocity was decreased from 375 µL/s to 38 µL/s, the acceleration was decreased from 1250 µL/s$^2$ to 200 µL/s$^2$, and all sample mixes were eliminated. Furthermore, the initial incubation at 45° C. in the standard RiboPrinter® System protocol was eliminated and the ACP incubation step was increased from 25 min to 45 min at 37° C.

E. coli, ATCC strain 51739, was cultured on brain heart infusion (BHI) agar overnight in an incubator at 37° C. The next day, colonies were picked using a RiboPrinter® System colony pick, available from Qualicon, Inc. Five picks were suspended in 300 µL of RiboPrinter® System sample buffer and the suspension was mixed using a vortexer. Thirty microliters of the cell suspension was added manually to each of the eight wells of the RiboPrinter® System sample carrier. The sample carrier was placed in the heat treatment station, supplied with the RiboPrinter® System, and heated at 80° C. for 10 min to inactivate the cells and to deactivate endogenous nuclease activity. When the sample carrier cooled after the heat treatment station treatment, it was loaded into the LDD Module. The DNA prep pack was modified by removing the digestion tablet and replacing it with 294 µL of 10× NEB Buffer 2 containing 10× BSA, both obtained from New England BioLabs, Inc. Fifty microliters of XbaI (20 Units/µL), purchased from New England BioLabs, Inc., was added to an empty RiboPrinter® System restriction enzyme vial, which was inserted into the DNA prep pack. The prep pack was loaded into the LDD module to initiate the LDD process.

The LDD module re-hydrated the ACP tablet and delivered 70 µL of the resulting solution to each sample. The samples were incubated at 37° C. for 45 min. After this time, the samples were heated to 70° C. for 25 min. Next, the LDD pipet removed 243 µL of the 10× restriction enzyme buffer (Buffer 2 plus BSA) and added it to the restriction enzyme vial containing the XbaI and the solution was mixed by aspiration. Then, the LDD pipet delivered 23 µL of the resulting XbaI solution to each sample, and the samples were incubated at 37° C. for three hours. After this time, 10 µL of the Ribo- Printer® System loading buffer (low salt formulation) was added to each sample well by the LDD pipet and the sample carrier was removed from the module.

The 1% agarose gel for the pulsed-field electrophoresis run was prepared in 0.5× tris-borate-EDTA (TBE) buffer according to the manufacturer's directions using pulsed-field grade agarose (purchased from Bio-Rad Laboratories). A 10 well comb, 14 cm wide and 0.75 mm thick, was used to form the wells in the gel. After the gel was prepared, sample lanes 1 and 10 were filled with plugs containing the lambda ladder DNA size marker, obtained from Bio-Rad Laboratories. This DNA size marker consists of concatemers of lambda DNA so that the fragments increase in size in approximately 48 kbp increments. The gel was then placed in the gel box of the Bio-Rad CHEF-DRII pulsed-field electrophoresis system, which was filled with 0.5× tris-borate-EDTA (TBE) buffer.

The processed liquid sample solutions were loaded into the electrophoresis gel using manual pipetting as follows. The sample solutions were mixed once very slowly by aspiration using a 200 μL Gilson Pipetman® to disperse the loading buffer and then added very slowly to wells 2 through 9 using the same Gilson Pipetman®. The recirculating pump of the PFGE apparatus was not turned on until approximately 30 minutes after the electrophoresis was started to allow the DNA molecules to enter the gel. This was done so the liquid samples would not be washed out of the wells.

The gel was run for 21 hours on the Bio-Rad CHEF-DRII pulsed-field electrophoresis system using a field strength of 6 V/cm, with initial and final switch times of 1 sec and 35 sec, respectively. After the run, the gel was removed from the gel box and placed in a solution containing ethidium bromide (0.5 μg/mL in water) for approximately one hour. The gel was then incubated in a tray containing Milli-Q water for approximately two hours to de-stain the gel. The gel was placed into the Bio-Rad Gel-Doc 1000 system to obtain an image of the gel, which is shown in FIG. 4.

Figure 4:
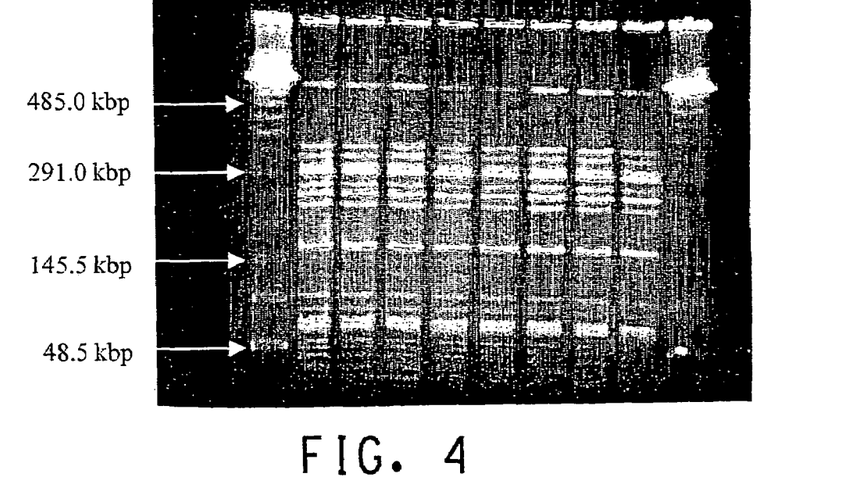
FIG. 4 shows the image of an agarose gel with the electrophoretic pattern of bacterial DNA from Example 1 obtained using optimized pipetting parameters.

As can be seen from FIG. 4, the reproducibility of the DNA patterns is excellent and no evidence of mechanical breakage is observed, as evidenced by the sharp bands and the absence of any in-lane smear. Mechanical breakage did not occur because of the gentle pipetting techniques that were used to minimize the forces acting on the DNA molecules.

Example 2

Processed Sample Liquid Solution of the Invention Compared with Conventional Plug In this example, conventional sample plugs were compared with the processed liquid sample solution of the invention using several strains of *E. coli*. The strains used were *E. coli* ATCC No. 51739, *E. coli* 0157:H7 strain ATCC No. 43889, and *E. coli* 0157:H7 strain 43894. These strains were cultured on BHI agar overnight at 37° C.

The processed sample liquid solution of the invention was prepared and transferred to an electrophoresis gel as described in Example 1. The conventional plugs were prepared according to published protocol using the CHEF bacterial genomic DNA plug kit obtained from Bio-Rad Laboratories. The cultures were sampled by taking 4 colony picks off the agar plates and placing the picks in 500 μL cell suspension buffer from the Bio-Rad kit. These cell suspensions and a 2% agarose solution were placed in a water bath thermostated at 50° C. The sample plugs were prepared by adding 500 μL of the agarose solution to 500 μL of each of the cell suspensions. The samples were mixed by aspiration using a pipet and were placed back into the water bath. Then, one plug mold (ten plugs) was prepared for each sample by adding 100 μL of the appropriate sample mixture to each well of one plug mold and the mold was placed in the refrigerator at 4° C. for 15 min. In this way, ten plugs were made for each strain being tested. The 10 sample plugs for each strain were removed from the molds and placed into 50 mL centrifuge tubes containing 5.0 mL of lysozyme solution (0.2 mL of Lysozyme, 2.5 mg/mL, in 5.0 mL of Lysozyme buffer). A screened cap was placed on each tube to facilitate solution removal. The plugs were incubated in the lysozyme solution overnight at 37° C.

The next day, the tubes containing the plugs were placed in an ice bath for 15-20 min to harden the plugs. Then, the lysozyme solution was drained from the tubes through the screened caps and 25 mL of 1× wash buffer was added. The tubes were rocked gently on a rocker platform for 10-15 min. The wash solution was drained and 2.5 mL of Proteinase K reaction buffer was added to each tube. One hundred microliters of Proteinase K was then added to each tube and the tubes were incubated overnight at 50° C.

The tubes were placed in an ice bath for 15-20 min. Next, the Proteinase K solution was drained from the tubes through the screened caps and 25 mL of 1× wash buffer was added to each tube. The tubes were then placed on a rocker platform and were rocked gently for one hour. After this time, the wash solution was removed and this wash process was repeated three more times to give a total of four washes. Then, 10 mL of 1× wash buffer was added to each tube. One plug was removed from each tube and the plugs were placed in separate 50 mL centrifuge tubes containing 25 mL of 0.1× wash buffer. The tubes were placed on a rocker platform and rocked gently for 30 min. The plugs were then transferred to separate 1.5 mL centrifuge tubes and 900 μL of 1× restriction enzyme buffer (NEB Buffer 2 containing 1× BSA) was added to each tube. The tubes were placed on the rocker platform for one hour. The buffer was removed from each tube using a pipet and 300 μL of fresh 1× restriction enzyme buffer was added to each tube. Then, 10 μL of XbaI restriction enzyme was added to each tube and the tubes were incubated at 37° C. overnight.

The next day, the tubes were placed in an ice bath for 15-20 min. The restriction enzyme solution was removed from each tube using a pipet and the plugs were washed with 1.0 mL of 1× wash buffer for 30 min on the rocker platform. This wash solution was removed from the tubes using a pipet and replaced with 1.0 mL of 0.5× TBE buffer and the tubes were rocked for 30 min.

Figure 5:
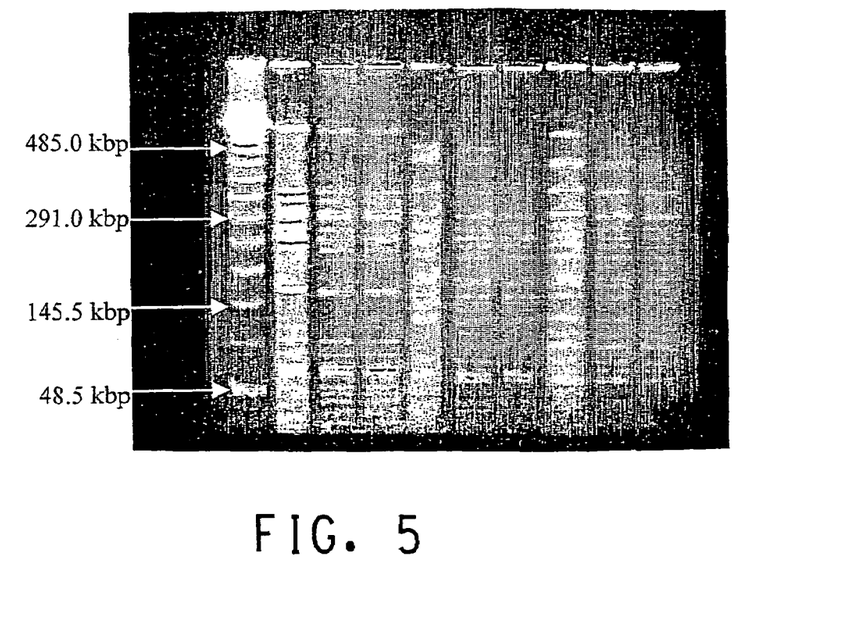
FIG. 5 shows the image of an agarose gel with the electrophoretic pattern of bacterial DNA from Example 2 comparing conventional sample plugs with processed liquid samples.

The agarose gel was prepared as described in Example 1 and sample lane 1 was filled with a plug containing the lambda ladder DNA size marker. Then, the sample plugs were loaded into the gel as follows: ATCC Strain No. 51739 in lane 2; ATCC Strain No. 43889 in lane 5; and ATCC Strain No. 43894 in lane 8. The gel was placed into the gel box of the Bio-Rad CHEF-DRII pulsed-field electrophoresis system, which was filled with 0.5× tris-borate-EDTA (TBE) buffer. The processed sample liquid solutions were loaded manually, as described in Example 1, in the two wells adjacent to the plug samples, i.e., ATCC Strain No. 51739 in lanes 3 and 4, ATCC Strain No. 43889 in lanes 6 and 7, and ATCC Strain No. 43894 in lanes 9 and 10. The PFGE conditions were the same as given in Example 1. The results of this experiment are shown in FIG. 5. As can be seen, the patterns obtained for the liquid samples are identical to those obtained with the conventional sample plugs.

Example 3

Figure 6:
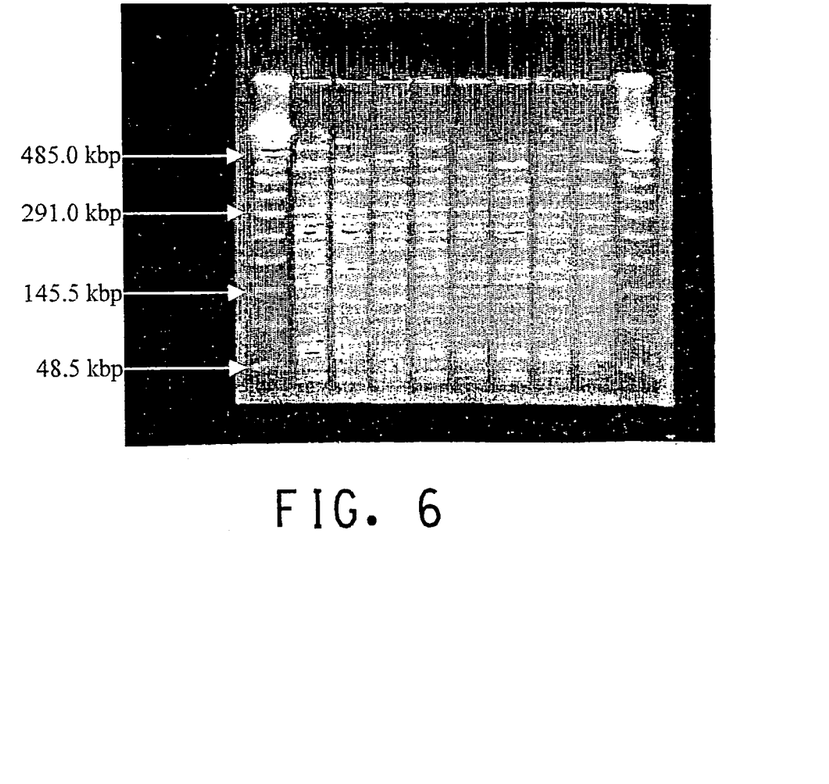
FIG. 6 shows the image of an agarose gel with the electrophoretic pattern of bacterial DNA from Example 3 obtained using optimized pipetting parameters.

Automated Treatment of Several E. coli 0157:H7 Strains Using Optimized Pipetting Parameters Eight strains of E. coli 0157:H7, isolated from several outbreaks, were cultured, treated, and transferred to an electrophoresis gel as described in Example 1. The results are shown in FIG. 6. As can be seen, eight distinct patterns were obtained and no mechanical breakage of the DNA was observed, as evidenced by the sharp bands and the absence of any in-lane smear.

Example 4

Determination of Operating Conditions to Minimize DNA Mechanical Breakage

Our original concept was that the long, processing-time deficiency of conventional methods could be overcome by working in a liquid medium entirely and that the problems of the past in breaking long DNA molecules in liquid handling could be avoided in the proper low force regime. That this concept was sound is shown by the previous examples. In this example, optimum reagent delivery parameters were experimentally determined using the RiboPrinter® System LDD module.

The process used with bacterial samples for automated pulsed-field gel electrophoresis analysis is given below. A diagram showing the transition region of the pipet tip is provided in FIG. 1, and the dimensions of the pipet tip used to deliver the reagents are as follows:

| | |
|---|---|
| Length | 141.0 +/− 0.25 mm (5.551 +/− 0.010 in) |
| Tip ID | 0.50 +/− 0.10 mm (0.020 +/− 0.004 in) |
| ID after transition | 1.60 +/− 0.10 mm (0.062 +/− 0.004 in) |

The geometry of a suitable sample well 6 is depicted in FIG. 2.

The wells of the sample carrier were initially filled with 30 µL of a suspension of bacterial cells in buffer, as described in Example 1. This step was done using manual pipetting. The sample carrier was then heated on the heat treatment station at 80° C. for 10 min. Some evaporation occurred during this step, reducing the sample volume to approximately 22 µL.

The sample carrier was then placed into the LDD Module and the process begun. The instrument was programmed to add 70 µL of an enzyme solution in buffer to each well. There was an incubation period, followed by a heat step at 70° C. for 25 min. This step was followed by a cool down period to return the temperature to 37° C. The second reagent addition was then made, consisting of an addition of 23 µL of an enzyme solution. This enzyme solution contained 8.5% glycerol, thus having a higher viscosity than an aqueous buffer, i.e., 1.64 cP at 25° C.

Next, another incubation was conducted, followed by addition of 10 µL of loading buffer, which is a fairly viscous solution. The actual viscosity of the loading buffer was 3.44 cP at 25° C.

For each reagent addition, the pipet tip was positioned between 3 mm and 4 mm from the bottom of the well.

After the last reagent addition, the samples were removed manually using very gentle pipetting and were added to the wells of the gel, as described in Example 1. The addition parameters that were tested for all three reagents are given below in Table I.

TABLE I

| Sample Well | Reagent Addition Velocity (µL/s) | Reagent Addition Acceleration (µL/s$^2$) |
|---|---|---|
| 1 | 38 | 200 |
| 2 | 116 | 2000 |
| 3 | 193 | 3800 |
| 4 | 271 | 5600 |
| 5 | 348 | 7400 |
| 6 | 426 | 9200 |
| 7 | 503 | 11000 |
| 8 | 581 | 12800 |

The velocity-time profile in our system is trapezoidal. The velocities given above are the maximum velocities.

Figure 7:
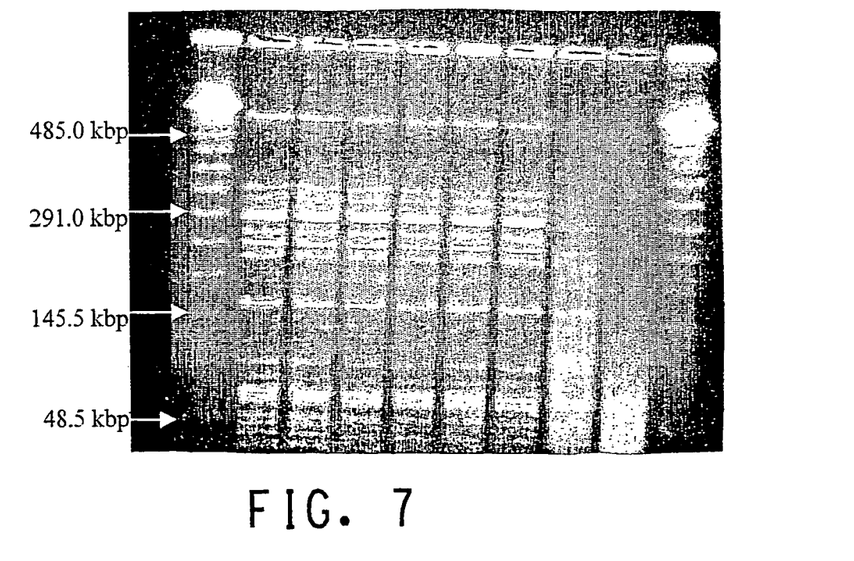
FIG. 7 shows the image of an agarose gel with the electrophoretic pattern of bacterial DNA from Example 4 obtained while determining operating conditions to minimize mechanical breakage of the DNA.

The results from this experiment are shown in FIG. 7. As can be seen in FIG. 7, no significant mechanical breakage of the DNA was evident in samples 1-6. The parameters for sample 7 gave significant mechanical breakage of the DNA fragments, as evidenced by the loss of bands and the in-lane smear. The sample 8 parameters gave almost total degradation of the DNA in the size range of interest (50 to 70 kbp) due to mechanical breakage. Therefore, controlling the reagent addition parameters to be less than those used in Sample 6 above will minimize the forces that cause mechanical breakage of the DNA molecules during sample treatment. The results of this experiment were not consistent. On some runs no mechanical breakage of DNA was observed at the highest reagent addition velocities and accelerations used, i.e., samples 7 and 8. These inconsistent results probably resulted from the normal variability of the automated process. For example, small changes in the position of the sample carrier, relative to its placement in the LDD module, result in variability of the pipet position relative to the sample wells during reagent delivery. This variability affects the flow patterns in the wells and therefore, the forces acting on the DNA molecules. However, the low reagent delivery and acceleration parameters used for sample 1, which are preferred, always gave good results, i.e., no significant mechanical breakage of the DNA molecules.

Example 5

Figure 8:
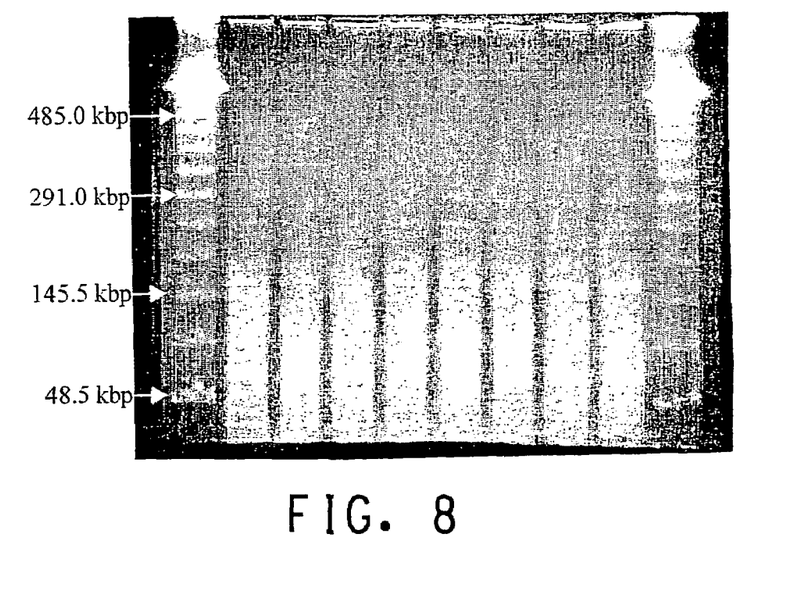
FIG. 8 shows the image of an agarose gel with the electrophoretic pattern of bacterial DNA from Example 5 obtained using the default RiboPrinter® System pipetting parameters.

Automated Treatment of Bacterial Cells Using Default RiboPrinter® System Pipetting Parameters This Example was done as described in Example 1, except that the default RiboPrinter® System pipet delivery velocity and acceleration were used, i.e., reagent delivery velocity of 375 µL/s with an acceleration of 1250 µL/s$^2$. The samples were also mixed several times by aspiration after reagent delivery. The results are shown in FIG. 8. As can be seen, there was significant degradation of the DNA caused by mechanical breakage, as evidenced by the loss of all bands above about 150 kbp and the in-lane smear below 150 kbp. This example demonstrates the need to carefully control the forces induced by reagent delivery and mixing.

Example 6

Manual Treatment of Bacterial Cells Using Low Force Pipetting

In the following example, all the pipetting was done manually. The RiboPrinter® System lysis deproteinization digestion (LDD) module was used only as a computer-controlled heating block. The pipet on the instrument was inactivated.

E. coli, ATCC strain 51739, was cultured on brain heart infusion (BHI) agar overnight in an incubator at 37° C. The next day, colonies were picked using a RiboPrinter® System colony pick. Five picks were suspended in 300 µL of RiboPrinter® System sample buffer and the suspension was mixed using a vortexer. Thirty microliters of the cell suspension was added to each of the eight wells of the RiboPrinter® System sample carrier. The sample carrier was placed in the heat treatment station, supplied with the RiboPrinter® System, and heated to 80° C. for 10 min to inactivate the cells and to deactivate endogenous nuclease activity.

The RiboPrinter® System was started by selecting a modified substitute enzyme batch (SEC batch), which had an extended digestion time, i.e., 37° C. for 180 min, from the operations pull-down menu and the batch was submitted to the instrument. The achromopeptidase (ACP) tablet in the RiboPrinter® System DNA prep pack was rehydrated with 990 µL of Milli-Q water and the solution was mixed by vortexing. After the sample carrier returned to room temperature after heat treatment station treatment, 70 µL of the ACP solution was added to each sample well using a 100 µL Gilson Pipetman®. The solution was added very slowly down the side of the sample wells to minimize the forces on the DNA molecules. The sample solutions were not mixed. The sample carrier was placed into the LDD module of the RiboPrinter® System and the other consumables were loaded, according to the manufacturer's directions, to begin the LDD process.

At the start of the LDD process, the samples were incubated at 42° C. for 15 min and then, at 37° C. for an additional 25 min to lyse the cells and digest cellular proteins. The samples were then heated to 70° C. for 25 min to deactivate the ACP enzyme. The restriction enzyme solution was prepared as follows. Fifty microliters of XbaI (20 Units/µL), purchased from New England BioLabs, Inc., was added to an empty RiboPrinter® System restriction enzyme vial. Then, 243 µL of 10× NEB Buffer 2 containing 10× BSA (both obtained from New England BioLabs, Inc.) was added to the vial containing the XbaI and the solution was mixed by repeated aspiration. After the samples cooled down following protease deactivation, twenty-three microliters of the XbaI solution was added to each sample using a 100 µL Gilson Pipetman®. The solution was added very gently down the side of the well and the samples were not mixed to minimize the forces on the DNA molecules. The samples were incubated at 37° C. for three hours. After this time, 10 µL of the RiboPrinter® System loading buffer (low salt formulation) was added to each sample well by slowly pipetting the solution down the side of the well to minimize the forces on the DNA molecules. The samples were not mixed. The sample carrier was then removed from the RiboPrinter® System instrument and the batch was terminated manually.

Figure 9:
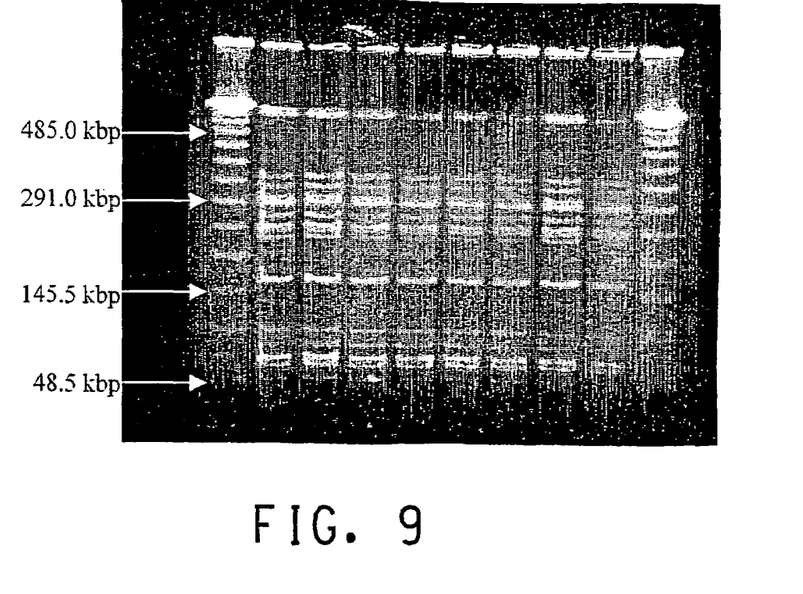
FIG. 9 shows the image of an agarose gel with the electrophoretic pattern of bacterial DNA from Example 6 obtained using low force manual pipetting.

The samples were loaded manually into the gel and the electrophoretic separation was run as described in Example 1. The resulting gel image is shown in FIG. 9. As can be seen in the figure, sharp bands with little evidence of mechanical breakage of the DNA were obtained.

Although illustrated and described above with reference to specific embodiments, the present invention is nevertheless not intended to be limited to the details shown. Rather, various modifications may be made in the details within the scope and range of equivalents of the claims and without departing from the spirit of the invention.

What is claimed is:

1. A process for preparing a processed sample liquid solution for molecular typing of bacteria using pulsed field gel electrophoresis, comprising the steps of:
   (a) treating a sample comprising a bacterial cell suspension in a non-shearing manner to produce a processed sample liquid solution comprising a mixture of DNA fragments extracted from said cell suspension, wherein at least one of said DNA fragments is greater than 200 kilobase pairs; wherein said treating comprises subjecting said cell suspension to lysis, deproteinization and digestion; and
   (b) transferring said processed sample liquid solution in a non-shearing manner directly to an electrophoresis medium for conducting pulsed field gel electrophoresis.

2. The process of claim 1 wherein said cell suspension comprises one or more cells suspended in a lysis buffer.

3. The process of claim 1 wherein said lysis and deproteinization comprises treatment with the enzyme achromopeptidase.

4. The process of claim 1 wherein said digestion comprises treatment with a restriction enzyme.

5. The process of claim 4 wherein said restriction enzyme is selected from the group consisting of XbaI, SfiI SmaI, NotI, ApaI, and AscI.

6. The process of claim 1 wherein said DNA fragments are 50 kilobase pairs to 1000 kilobase pairs.

7. The process of claim 1 wherein said step (a) is automated.

8. The process of claim 1 wherein said step (b) is automated.

9. The process of claim 1 wherein said steps (a) and (b) are automated.

10. The process of claim 1 wherein said electrophoresis medium is an electrophoresis gel.

11. The process of claim 1 wherein said electrophoresis medium is a well of an electrophoresis gel.

12. The process of claim 1 wherein said electrophoresis medium is a viscous sieving solution.

13. A process for separating a mixture of DNA fragments extracted from a bacterial cell suspension for molecular typing of bacteria using pulsed-field gel electrophoresis, comprising the steps of:
   (a) treating a sample comprising a bacterial cell suspension in a non-shearing manner to produce a processed sample liquid solution comprising a mixture of DNA fragments extracted from said cell suspension, wherein at least one of said DNA fragments is greater than 200 kilobase pairs; wherein said treating comprises subjecting said cell suspension to lysis, deproteinization and digestion;
   (b) transferring said processed sample liquid solution in a non-shearing manner directly to an electrophoresis medium; and
   (c) separating said mixture of DNA fragments by conducting pulsed field gel electrophoresis.

14. The process of claim 13 wherein said cell suspension comprises one or more cells suspended in a lysis buffer.

15. The process of claim 13 wherein said DNA fragments are 50 kilobase pairs to 1000 kilobase pairs.

16. The process of claim 13 wherein said step (a) is automated.

17. The process of claim 13 wherein said step (b) is automated.

18. The process of claim 13 wherein said steps (a) and (b) are automated.

19. The process of claim 13 wherein said processed sample liquid solution is transferred to a well of said electrophoresis medium.

20. The process of claim 13 wherein said electrophoresis is pulsed-field capillary electrophoresis.

21. The process of claim 13 wherein said lysis and deproteinization comprises treatment with the enzyme achromopeptidase.

22. The process of claim 13 wherein said digestion comprises treatment with a restriction enzyme.

23. The process of claim 22 wherein said restriction enzyme is selected from the group consisting of XbaI, SfiI, SmaI, NotI, ApaI, and AscI.

* * * * *